United States Patent [19]

Sheppard et al.

[11] Patent Number: 5,693,741

[45] Date of Patent: Dec. 2, 1997

[54] LIQUID MOLDING COMPOUNDS

[75] Inventors: Clyde H. Sheppard, Bellevue, Wash.; Hyman R. Lubowitz, Rolling Hills Estates, Calif.

[73] Assignee: The Boeing Company, Seattle, Wash.

[21] Appl. No.: 168,289

[22] Filed: Mar. 15, 1988

[51] Int. Cl.$^6$ .............. C07D 209/56; C07D 491/00; C08G 73/10

[52] U.S. Cl. .............. 528/183; 252/182.23; 252/183.11; 428/411.1; 428/473.5; 428/474.4; 548/428; 548/429; 548/431; 548/433; 548/435

[58] Field of Search ............... 548/435, 433, 548/431, 429, 428; 252/182.23, 183.11; 524/94; 428/473.5, 474.4; 525/420; 528/183

[56] References Cited

U.S. PATENT DOCUMENTS

| | | |
|---|---|---|
| 4,414,269 | 11/1983 | Lubowitz et al. ............... 548/435 |
| 4,460,783 | 7/1984 | Nishikawa et al. ............. 548/435 |
| 4,476,184 | 10/1984 | Lubowitz et al. ............... 548/435 |
| 4,515,962 | 5/1985 | Renner ............................ 548/435 |
| 4,555,563 | 11/1985 | Hefner, Jr. et al. ............. 548/435 |
| 4,604,437 | 8/1986 | Renner ............................ 548/435 |
| 4,728,742 | 3/1988 | Renner ............................ 548/435 |
| 4,739,030 | 4/1988 | Lubowitz et al. ............... 548/435 |
| 4,739,075 | 4/1988 | Odagiri et al. .................. 548/435 |
| 4,851,501 | 7/1989 | Lubowitz et al. ............... 528/170 |
| 4,868,270 | 9/1989 | Lubowitz et al. ............... 528/170 |
| 4,876,328 | 10/1989 | Lubowitz et al. ............... 528/322 |

*Primary Examiner*—Richard D. Lovering
*Attorney, Agent, or Firm*—John C. Hammar

[57] ABSTRACT

Low molecular weight resins that usually are aliphatic and that include crosslinking thermal functional groups are useful as liquid molding compounds for reaction injection molding or resin transfer molding. The compounds eliminate the need to handle solvents when preparing thermoset composites.

67 Claims, No Drawings

LIQUID MOLDING COMPOUNDS

TECHNICAL FIELD

The present invention relates to a family of relatively low-viscosity monomers that can be used in injection molding to fabricate high performance, advanced composites without the use of solvents. The composite parts are generally thermoset compositions with stable melts at moderate temperatures. Diamine diluents can be added to the monomers to prepare block copolymers upon curing.

BACKGROUND OF THE INVENTION

Recently, chemists have sought to synthesize oligomers for high performance advanced composites suitable for aerospace applications. These composites should exhibit solvent resistance; be tough, impact resistant, and strong; be easy to process; and be thermoplastic. Oligomers and composites that have thermo-oxidative stability and, accordingly, can be used at elevated temperatures are particularly desirable.

While epoxy-based composites are suitable for many applications, their brittle nature and susceptibility to thermal or hydrolytic degradation make them inadequate for many aerospace applications, especially those applications which require thermally stable, tough composites. Accordingly, research has recently focused on polyimide composites to achieve an acceptable balance between thermal stability, solvent resistance, and toughness. Still the maximum temperatures for use of the polyimide composites, such as PMR-15, are about 600°–625° F., since they have glass transition temperatures of about 690° F. PMR-15 still suffers, however, from brittleness.

There has been a progression of polyimide sulfone compounds synthesized to provide unique properties or combinations of properties. For example, Kwiatkowski and Brode synthesized maleic-capped linear polyarylimides as disclosed in U.S. Pat. No. 3,839,287. Holub and Evans synthesized maleic- or nadic-capped, imido-substituted polyester compositions as disclosed in U.S. Pat. No. 3,729,446. We synthesized thermally stable polysulfone oligomers as disclosed in U.S. Pat. No. 4,476,184 or U.S. Pat. No. 4,536,559, and have continued to make advances with polyetherimidesulfones, polybenzoxazolesulfones, polybutadienesulfones, and "star" or "star-burst" multidimensional oligomers. We have shown surprisingly high glass transition temperatures yet reasonable processing and desirable physical properties in many of these oligomers and their composites.

Polybenzoxazoles and other heterocycle oligomers, such as those disclosed in our copending applications U.S. Ser. Nos. 116,592, now U.S. Pat. No. 4,965,336, (to Lubowitz & Sheppard) and 121,964, now U.S. Pat. No. 4,868,270, (to Lubowitz, Sheppard, and Stephenson), may be used at temperatures up to about 750°–775° F., since these composites have glass transition temperatures of about 840° F. Some aerospace applications need composites which have even higher use temperatures while maintaining toughness, solvent resistance, ease of processing, formability, strength, and impact resistance.

Multidimensional oligomers, such as disclosed in our copending applications U.S. Ser. Nos. 810,817 now abandonedly and 000,605, now U.S. Pat. No. No. 5,210,213, are easier to process than some advanced composite oligomers since they can be handled at lower temperatures. Upon curing, however, the oligomers crosslink (homopolymerize) through their end caps so that the thermal resistance of the resulting composite is markedly increased with only a minor loss of stiffness, matrix stress transfer (impact resistance), toughness, elasticity, and other mechanical properties. Glass transition temperatures above 950° F are achievable.

Commercial polyesters, when combined with well-known diluents, such as styrene, do not exhibit satisfactory thermal and oxidative resistance to be useful for aircraft or aerospace applications. Polyarylesters are often unsatisfactory, also, since the resins often are semicrystalline which may makes them insoluble in laminating solvents, intractable in fusion, and subject to shrinking or warping during composite fabrication. Those polyarylesters that are soluble in conventional laminating solvents remain so in composite form, thereby limiting their usefulness in structural composites. The high concentration of ester groups contributes to resin strength and tenacity, but also makes the resin susceptible to the damaging effects of water absorption. High moisture absorption by commercial polyesters can lead to distortion of the composite when it is loaded at elevated temperature.

High performance, aerospace, polyester advanced composites, however, can be prepared using crosslinkable, end capped polyester imide ether sulfone oligomers that have an acceptable combination of solvent resistance, toughness, impact resistance, strength, processibility, formability, and thermal resistance. By including Schiff base (—CH═N—), imidazole, thiazole, or oxazole linkages in the oligomer chain, the linear, advanced composites formed with polyester oligomers of our copending application U.S. Ser. No. 726,259, now abandoned can have semiconductive or conductive properties when appropriately doped.

Conductive and semiconductive plastics have been extensively studied (See, e.g., U.S. Pat. Nos. 4,375,427; 4,338, 222; 3,966,987; 4,344,869; and 4,344,870), but these polymers do not possess the blend of properties which are essential for aerospace applications. That is, the conductive polymers do not possess the blend of (1) toughness, (2) stiffness, (3) elasticity, (4) ease of processing, (5) impact resistance (and other matrix stress transfer capabilities), (6) retention of properties over a broad range of temperatures, and (7) high temperature resistance that is desirable on aerospace advanced composites. The prior art composites are often too brittle.

Thermally stable multidimensional oligomers having semiconductive or conductive properties when doped with suitable dopants are also known and are described in our copending applications (including U.S. Ser. No. 773,381 to Lubowitz, Sheppard and Torre). The linear arms of the oligomers contain conductive linkages, such as Schiff base (—N═CH—) linkages, between aromatic groups. Sulfone and ether linkages are interspersed in the arms. Each arm is terminated with a mono- or difunctional end cap (i.e. an end cap having one or two crosslinking functionalities) to allow controlled crosslinking upon heat-induced or chemically-induced curing. Other "semiconductive" oligomers are described in our other copending applications.

Polyamide oligomers and blends are described in our copending applications U.S. Ser. No. 046,202, now U.S. Pat. No. 4,935,523, and 051,884, now U.S. Pat. No. 4,847,333, and polyetherimide oligomers and blends are described in our copending application U.S. Ser. No. 016,703, now U.S. Pat. No. 4,851,495.

Polyamideimides are generally injection-moldable, amorphous, engineering thermoplastics which absorb water (swell) when subjected to humid environments or immersed in water. Polyamideimides are generally described in the following patents: U.S. Pat. Nos. 3,658,938; 4,628,079;

4,599,383; 4,574,144; or 3,988,344. The thermal integrity and solvent-resistance can be greatly enhanced by capping amideimide backbones with monomers that present one or two crosslinking functionalities at each end of the oligomer, as described, in our copending application U.S. Ser. No. 092,740 now abandoned, but the injection molding capability probably is lost.

The high performance resins that we described in our earlier applications and summarized here can be processed into prepregs, but require that solvents be used for this processing. The management of the solvent during the manufacturing process accordingly, presents problems, such as ease of handling, convenience, cost, waste management, and personal safety. These problems are alleviated in a process that can eliminate the solvents.

While prepreg layup and curing is cost effective for manufacturing one class of aerospace parts, an injection molding compound in liquid form would allow the manufacture of large parts (including complex curvature) quickly and with comparatively low investment. Composite molds may be used when the molding compounds cure at relatively low pressures. Reinforced parts can be made in the molds by including filaments or fabrics in the mold. Injection molding eliminates the high labor cost of prepreg layup that is incurred for complex shapes, especially those requiring precise shapes to within a close tolerance. Often milling is required to make such shapes, with the resultant equipment (capital) and labor costs.

Several resins for reaction injection molding (RIM) or resin transfer molding (RTM) have been developed, including urethanes, esters, ureas, acrylesterols, triazathanes, and cyclopentadienes (i.e., PDCPD, such as METTON polymers available from Hercules, Inc.). These molding resins, however, often exhibit premature gelling, a problem that is overcome with the family of liquid molding compounds of the present invention.

SUMMARY OF THE INVENTION

Liquid molding compounds of the present invention are suitable for reaction injection molding (RIM) or resin transfer molding (RTM) to form thermoset composites with or without fiber reinforcement. The compounds are free of solvents and can be quickly cured at modest temperatures and pressures to produce rigid composites that offer a wide range of flexibility and resilience. The liquid molding compounds are characterized by including crosslinking (i.e. unsaturated hydrocarbon) groups at the ends of the polymer backbone. The liquid molding compounds comprise a compound of the general formula

[(D<sub>i</sub>─)<sub>n</sub>─Q wherein $D_i$ are the crosslinking groups. The crosslinking groups generally are radicals selected from the group consisting of:

D<sub>i</sub>─φ─ wherein i=1 or 2 (i.e. mono- or difunctional);

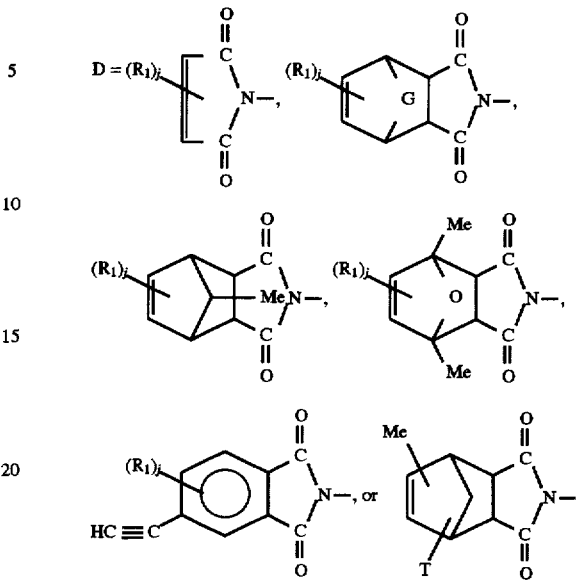

$R_1$=lower alkyl, lower alkoxy, aryl, aryloxy, substituted alkyl, substituted aryl (the substituents including hydroxyl or halo groups), halogen, or mixtures thereof;
j=0, 1 or 2;
G=—CH<sub>2</sub>—, —O—, —S—, —SO<sub>2</sub>—, —SO—, —CO—, —CHR—, or —CR<sub>2</sub>—;
T=methallyl or allyl;
Me=methyl; and
R=hydrogen, lower alkyl, or phenyl
and, preferably, wherein D=

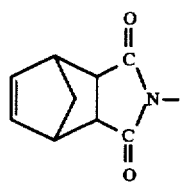

In one embodiment, the crosslinking groups are radicals selected from the group consisting of D<sub>i</sub>—φ— wherein D and i, are as defined above and φ=phenylene. The phenyl group may be replaced with a pyrimidine group, but these compounds are not preferred.

The compounds are generally polyethers made from polyether diols or triols, such as polypropylene glycol triol of the general formula:

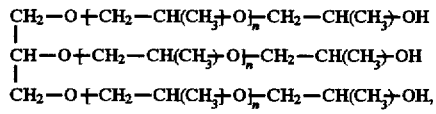

condensed with an acid halide cap of the formula: D<sub>i</sub>—φ—COX or a nitro cap of the formula D<sub>i</sub>—φ—NO<sub>2</sub>. Other suitable reactants, include esters, urethanes, amides, imides, ureas, and mixtures (or blends) thereof, especially those reactants, such as oxypropylene triamine, that have aliphatic backbones comparable to the triol described above. The cap may include a hydroxyl, an amine, an acid halide, or a nitro functionality as necessary to complete the reaction. Anhydrides containing the unsaturation of the D radical may also be used, especially with oxypropylene triamine.

BEST MODE CONTEMPLATED FOR MAKING AND USING THE INVENTION

The present invention of liquid molding resins describes a family of relatively low-viscosity oligomers that are suitable for reaction injection molding (RIM) or resin transfer molding (RTM) at modest temperatures and pressures to form high performance, thermoset composites without the use of the solvents that are customarily required to make comparable composites from prepregs. The composites are generally rigid but they offer a wide range of flexibility and resilience.

The liquid molding compounds include mono- or difunctional, crosslinking groups (i.e., groups having one or two crosslinking sites) of the same nature as our earlier high performance resins. These groups improve the solvent resistance and thermo-oxidative stability of the composites. The compounds also include polymeric backbones of ethers, esters, urethanes, amides, imides, ureas, or mixtures (i.e. blends) of two or more of these compounds. The liquid molding compounds are prepared by reacting the crosslinking end-cap monomers with polyether diols or triols, esters, or the like, or in simultaneous condensation reactions that include the precursors of such backbones and suitable end-cap monomers.

The crosslinking end cap monomers have hydrocarbon unsaturation and generally include a radical selected from the group consisting of:

wherein i=1 or 2;

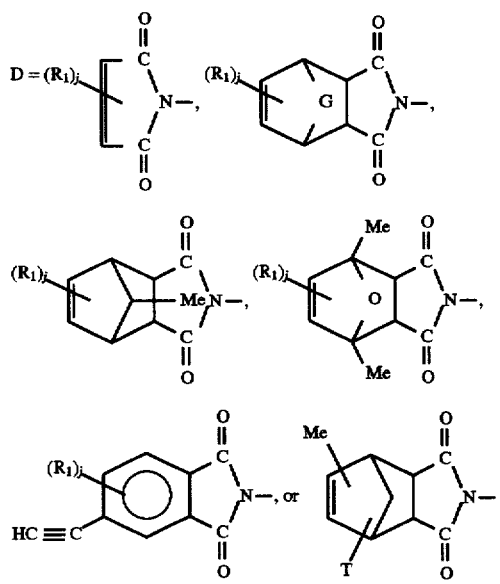

R₁=lower alkyl, lower alkoxy, aryl aryloxy, substituted alkyl, substituted aryl (the substituents including hydroxyl or halo groups), halogen, or mixtures thereof;
G=—SO₂—, —S—, —O—, or —CH₂—, —CO—, —SO—, —CHR—, or —CR₂—;
i=1 or 2;
j=0, 1 or 2;
T=methallyl or allyl;
Me=methyl; and
R=hydrogen, lower alkyl, or phenyl.
The cross-linking end cap monomers preferably include phenylene, i.e., have the formula D$_i$—φ—. A particularly preferred end-cap is:

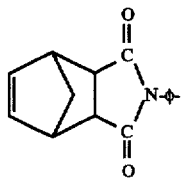

because of its relatively low cost and its relatively low activation (i.e. curing) temperature. The resulting thermoset composites have relatively high thermal stability.

Suitable ether precursors are characterized by the aliphatic triol, polypropylene glycol triol of the general formula:

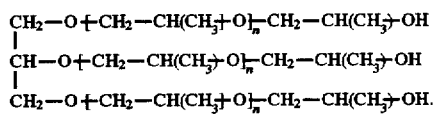

Ether diols or triols of this general type can be reacted with D$_i$—φ—COX to form capped ethers through the —OH/—COX ester condensation. Compounds of the formula: D$_i$—φ—COX are readily prepared from the corresponding anhydrides by condensation with amino- or diamino benzoic acid, as explained in U.S. Pat. No. 4,604,437. Alternatively, the ether precursors can be condensed with a nitro end cap monomer formed by reacting the anhydrides with nitroaniline to form an ether linkage between the precursor and the cap.

Although not preferred because of cost and complexity, the acid halide end-cap monomer can be made by condensing the anhydrides with a pyrimidine of the formula:

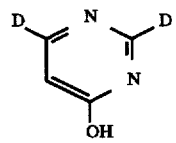

The precursor amines are describes in U.S. Pat. No. 3,461,461. The resulting intermediate can be reacted with nitrobenzoic acid halide or halobenzoic acid halide to form an acid halide end-cap monomer of the formula:

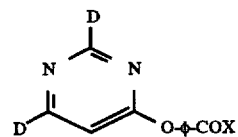

Polyamines, such as polyoxypropylene triamine (a counterpart of the propylene glycol triol) can be reacted directly with the anhydrides to form imide caps. Alternately, the terminal amino groups can be condensed with —COX of the end cap monomer to form an amide linkage. The absence of a phenyl radical adjacent the hydrogen unsaturation in the polyamine/anhydride condensation may impact the performance and physical properties of the resulting composites.

Moldable ureas can also be prepared by reacting an aliphatic, or aromatic, or aliphatic and aromatic diamine, such as phenylenediamine, with an anhydride used to form the D$_i$—φ— groups, such as:

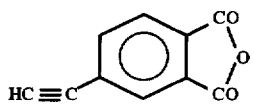

and a compound of the formula:

to form a capped reactive polyurea of the general formula:

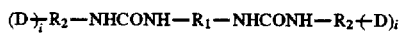

wherein i=1 or 2;

$R_2$=an aliphatic or aromatic residue of the diamine; (e.g., —φ— if phenylene diamine is used) and $R_1$=an aliphatic or aromatic residue.

The OCN—$R_1$—NCO compounds are described in U.S. Pat. No. 4,599,383, and generally include aliphatic segments. Generally an aliphatic diamine would also be used.

Polyoxypropylene triamine can be reacted with OCN—$R_1$—NCO, a diamine, and a suitable end cap to form a liquid molding compound. In this case, $R_1$ is generally a lower alkyl of less than about five carbon atoms, and the diamine is a lower alkyl diamine.

Preferably, any of the liquid molding compounds has an average formula weight below about 5000, and, generally, as low as about 1000.

The liquid molding compounds of the present invention can be improved by blending them with reactive diluents. Suitable diluents are aliphatic diamines, including, for example, 1,8-diaminooctane; 1,7-diaminoheptane; 1-5-diaminopentane; or 1,3-diaminopropane (i.e., diaminoalkyls). During curing, diamines of this type can react with the liquid molding compounds to form block copolymers.

The corresponding anhydrides used for direct reaction with the polyamines or for preparation of the nitro, acid halide, or phenol end cap monomers, of course, are selected from the group consisting of:

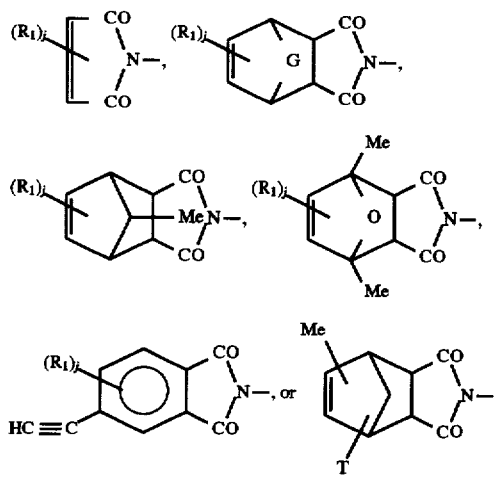

wherein $R_1$, G, Me, T, and j are as previously defined. In the direct condensation of the polyamines and anhydrides, only one crosslinking site is available at each chain terminus.

The polyols, such as polypropylene glycol triol, can have their chains extended by the nitro/phenol condensation using dinitro compounds. The end cap monomer in this case usually will be an imidophenol. Suitable dinitro compounds can be prepared, for example, by reacting MCTC (i.e., 5-(2,5-diketotetrahydro-furyl)-3-methyl-cyclohexene-1,2-dicarboxylic anhydride) with nitroaniline. Of course, other aliphatic dinitro compounds can be used, or an aromatic segment (particularly if it is short) may be incorporated into the liquid molding compound. Further chain extension can be achieved by adding dialcohols to the condensation mixture. Such chain extension, however, is likely to lead to the formation of undesirable, high-average-formula-weight oligomers. Therefore, usually the polyol will be condensed directly with the acid halide or nitro end cap monomer to form the product.

To limit the average formula weight of the products, the polyamines are generally condensed directly with the end cap anhydrides. Chain extension, however, can occur by using aliphatic dianhydrides, such as MCTC, and an imidophenylamine end cap monomer; by further extension with a dianhydride, a diamine, and a suitable end cap monomer; by using a dicarboxylic acid halide and an imidophenylamine end cap monomer, or in other ways known to those of ordinary skill in the art based upon this description.

It may be possible to make liquid molding compounds simply by reacting the OCN—$R_1$—NCO compounds directly with imidophenylamine end cap monomers.

The liquid molding compounds of the present invention may be blends of the crosslinking oligomers and coresponding, compatible, noncrosslinking polymers. For example, the polyols can be condensed with a nitro end cap monomer and nitrobenzene to form a mixture of capped and uncapped molecules that still might provide the desired molding properties. It probably would be better, however, to blend the oligomer with a quenched polyol rather than to conduct the syntheses simultaneously.

The liquid molding compounds or blends can be mixed with reinforcing additives prior to or during injection to produce reinforced composites. The additives can be in continuous (fiber) or discontinuous (chopped or whisker) form and may be ceramic, organic, carbon (graphite), or glass as desired for the particular application.

Blends can improve the impact resistance of the cured composites without deleterious loss of solvent resistance (gained through the crosslinking caps). A 50—50 molar blend of the oligomer and polymer is probably the most desirable blend, but the ratio can be adjusted to provide the desired physical properties in the composite.

It is probably nonessential that the oligomer and polymer have identical repeating units. They need only be compatible when mixed. The polyethers might be mixed with polyesters, polyamides, or other polymers without loss of the molding properties.

While preferred embodiments have been described, those skilled in the art will recognize modifications or variations which might be made without departing from the inventive concept. Therefore, the description and claims should be interpreted liberally to cover the disclosed embodiments and their full range of equivalents with only such that limitation which is necessary in view of the pertinent prior art.

We claim:

1. A composition comprising a liquid molding compound suitable for preparing injection-molded, high performance composites, the liquid molding compound having the general formula:

wherein i=2;

w=2 or 3;

D=a hydrocarbon radical having an unsaturated functionality selected from the group consisting of:

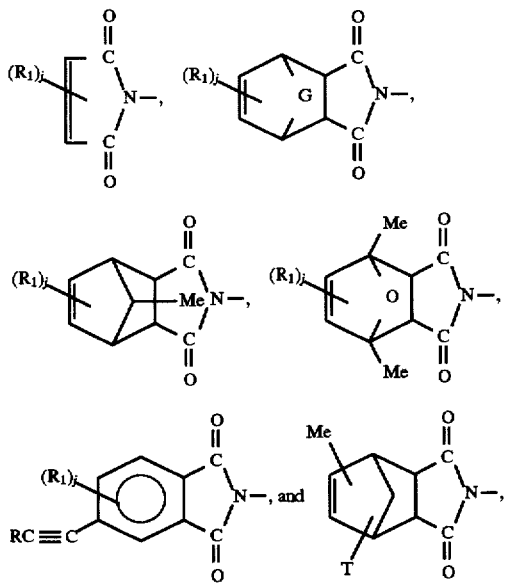

$R_1$=lower alkyl, aryl, substituted alkyl, substituted aryl, lower alkoxy, aryloxy, halogen, or mixtures thereof;

G=—CH$_2$—, —O—, —S—, —SO$_2$—, —SO—, —CO—, —CHR—, or —CR$_2$—;

j=0, 1 or 2;

T=allyl or methallyl;

Me=methyl;

Q=a hydrocarbon residue containing aliphatic groups connected by ether, ester, urethane, urea, amide, or imide linkages; and R=hydrogen, lower alkyl, or phenyl, wherein the compound can be used in injection molding without the need of solvents.

2. The composition of claim 1 further comprising a diluent.

3. The composition of claim 2 wherein the diluent is a diamine.

4. The composition of claim 3 wherein the diamine is an alkyl diamine having about 3–10 carbon atoms.

5. The composition of claim 1 wherein Q comprises a residue of polypropylene glycol triol.

6. The composition of claim 5 further comprising an aliphatic alkyl diamine diluent having about 3–10 carbon atoms.

7. The composition of claim 5 wherein

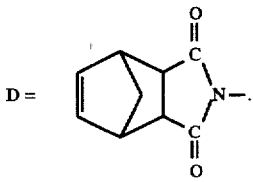

8. The composition of claim 1 wherein Q includes a residue of polyoxypropylene triamine.

9. The composition of claim 1 wherein Q includes a polyurea radical of the general formula:

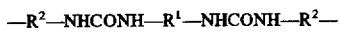

wherein $R^1$ and $R^2$=aliphatic or aromatic hydrocarbon residues.

10. The composition of claim 1 wherein

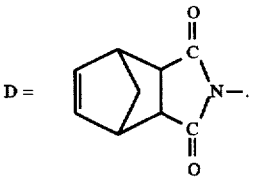

11. The composition of claim 1 having the general formula:

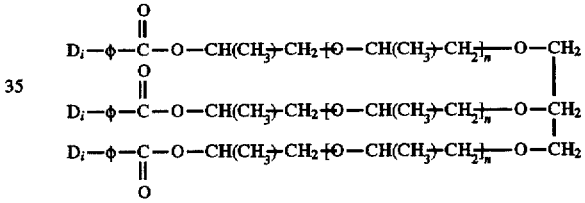

wherein $\phi$ phenylene.

12. The composition of claim 11 further comprising an alkyl diamine diluent.

13. The composition of claim 11 wherein

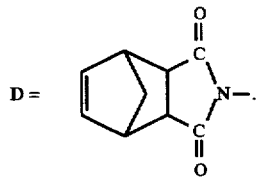

14. The composition of claim 13 wherein n is selected such that the liquid molding compound has an average formula weight below about 5000.

15. The composition of claim 13 wherein n is selected such that the liquid molding compound has an average formula weight of about 1000.

16. The composition of claim 13 further comprising an alkyl diamine diluent.

17. The composition of claim 11 wherein n is selected such that the liquid molding compound has an average formula weight below about 5000.

18. The composition of claim 11 wherein n is selected such that the liquid molding compound has an average formula weight of about 1000.

19. The composition of claim 1 wherein Q includes a hydrocarbon residue containing aliphatic groups connected by ether linkages.

20. The composition of claim 1 wherein Q includes a hydrocarbon residue containing aliphatic groups connected by ester linkages.

21. The composition of claim 1 wherein Q includes a hydrocarbon residue containing aliphatic groups connected by urethane linkages.

22. The composition of claim 1 wherein Q includes a hydrocarbon residue containing aliphatic groups connected by urea linkages.

23. The composition of claim 1 wherein Q includes a hydrocarbon residue containing aliphatic groups connected by amide linkages.

24. The composition of claim 1 wherein Q includes a hydrocarbon residue containing aliphatic groups connected by imide linkages.

25. The composition of claim 1 wherein i=2

D=a hydrocarbon radical having an unsaturated functionality selected from the group consisting of:

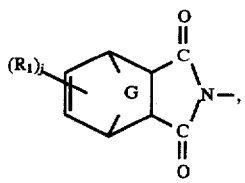

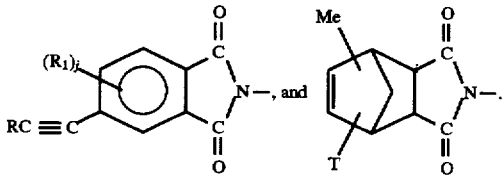

$R_1$=lower alkyl, aryl, substituted alkyl, substituted aryl, lower alkoxy, aryloxy, halogen, or mixtures thereof;

j=0, 1 or 2;

T=allyl or methallyl; and

Me=methyl.

26. The composition of claim 1 and a reinforcing additive in fiber or particulate form.

27. A composite formed by curing the compound of claim 1.

28. A composite formed by curing the compound of claim 2.

29. A composite formed by curing the compound of claim 11.

30. A composite formed by curing the compound of claim 26.

31. A blend comprising the compound of claim 1 and a compatible, noncrosslinking polymer.

32. The blend of claim 31 further comprising a reinforcing additive in fiber or particulate form.

33. The blend of claim 32 further comprising a diluent.

34. The blend of claim 31 further comprising a diluent.

35. A composite formed by curing the blend of claim 31.

36. A composition comprising a liquid molding compound suitable for preparing injection-molded, high performance composites, the liquid molding compound having the general formula:

wherein i=1 or 2 w=3;

D=a hydrocarbon radical having an unsaturated functionality selected from the group consisting of:

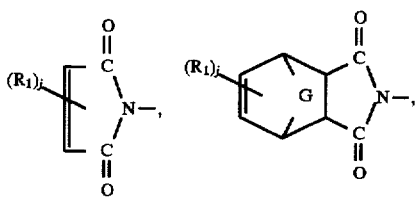

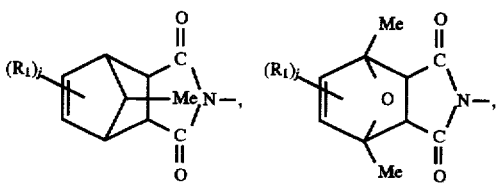

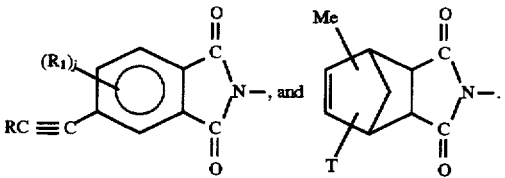

$R_1$=lower alkyl, aryl, substituted alkyl, substituted aryl, lower alkoxy, aryloxy, halogen, or mixtures thereof;

G=—$CH_2$—, —O—, —S—, —$SO_2$—, —SO—, —CO—, —CHR—, or —$CR_2$—;

j=0, 1 or 2;

T=allyl or methallyl;

Me=methyl;

Q=a hydrocarbon residue containing aliphatic groups connected by ether, ester, urethane, urea, amide, or imide linkages; and R=hydrogen, lower alkyl, or phenyl, wherein the compound can be used in injection molding without the need of solvents.

37. The composition of claim 36 comprising a diluent.

38. The composition of claim 37 wherein the diluent is an alkyl amine having about 3–10 carbon atoms.

39. The composition of claim 36 wherein Q includes a residue of polypropylene glycol triol.

40. The composition of claim 36 wherein Q includes a residue of polyoxy propylene triamine.

41. The composition of claim 40 further comprising an alkyl amine diluent having about 3–10 carbon atoms.

42. The composition of claim 36 wherein Q includes a polyurea radical of the general formula:

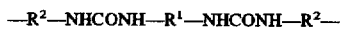

wherein $R^1$ and $R^2$=aliphatic or aromatic hydrocarbon residues.

43. The composition of claim 36 wherein the liquid molding compound has the general formula:

$$D_i-\phi-\overset{O}{\underset{\|}{C}}-O-CH(CH_3)-CH_2+O-CH(CH_3)-CH_2\underset{n}{+}O-CH_2$$
$$D_i-\phi-\overset{O}{\underset{\|}{C}}-O-CH(CH_3)-CH_2+O-CH(CH_3)-CH_2\underset{n}{+}O-CH$$
$$D_i-\phi-\overset{O}{\underset{\|}{C}}-O-CH(CH_3)-CH_2+O-CH(CH_3)-CH_2\underset{n}{+}O-CH_2$$

wherein φ=phenylene.

44. The composition of claim 43 wherein

D = [structure showing norbornene-fused imide group]

45. A liquid molding compound suitable for preparing injection-molded, high performance composites having the general formula:

$$[(D)_i-\phi-]_w-Q$$

wherein i=2
w=2 or 3;
D=is a hydrocarbon radical selected from the group consisting of:

[structures showing various imide-containing groups with (R₁)ⱼ substituents]

R₁=lower alkyl, aryl, substituted alkyl, substituted aryl, lower alkoxy, aryloxy, halogen, or mixtures thereof;
G=—CH₂—, —O—, —S—, —SO₂—, —SO—, —CO—, —CHR—, or —CR₂—;
j=0, 1 or 2;
T=allyl or methallyl;
Me=methyl;
Q=a hydrocarbon residue containing aliphatic groups connected by ether, ester, urethane, urea, amide, or imide linkages; and R=hydrogen, lower alkyl, or phenyl,
φ=phenylene
wherein the compound can be used in injection molding without the need of solvents.

46. The compound of claim 45 wherein w3.

47. A composition comprising the compound of claim 46 and an effective amount of an alkyl amine diluent having about 3–10 carbon atoms.

48. The compound of claim 45 wherein Q includes a residue of polypropylene glycol triol or polyoxy propylene triamine.

49. The compound of claim 45 wherein Q includes a hydrocarbon residue containing aliphatic groups connected by ether linkages.

50. The compound of claim 45 wherein Q includes a hydrocarbon residue containing aliphatic groups connected by ester linkages.

51. The compound of claim 45 wherein Q includes a hydrocarbon residue containing aliphatic groups connected by urethane linkages.

52. The compound of claim 45 wherein Q includes a hydrocarbon residue containing aliphatic groups connected by urea linkages.

53. The compound of claim 45 wherein Q includes a hydrocarbon residue containing aliphatic groups connected by amide linkages.

54. The compound of claim 45 wherein Q includes a hydrocarbon residue containing aliphatic groups connected by imide linkages.

55. The compound of claim 45 having the general formula:

$$D_i-\phi-\overset{O}{\underset{\|}{C}}-O-CH(CH_3)-CH_2+O-CH(CH_3)-CH_2\underset{n}{+}O-CH_2$$
$$D_i-\phi-\overset{O}{\underset{\|}{C}}-O-CH(CH_3)-CH_2+O-CH(CH_3)-CH_2\underset{n}{+}O-CH$$
$$D_i-\phi-\overset{O}{\underset{\|}{C}}-O-CH(CH_3)-CH_2+O-CH(CH_3)-CH_2\underset{n}{+}O-CH_2$$

wherein φ=phenylene.

56. The compound of claim 55 wherein

D = [structure showing norbornene-fused imide group]

57. The compound of claim 55 wherein n is selected such that the liquid molding compound has an average formula weight below about 5000.

58. The compound of claim 55 wherein n is selected such that the liquid molding compound has an average formula weight of about 1000.

59. The compound of claim 45 wherein D=

[structure: norbornene-fused imide with D= label]

60. The compound of claim 45 wherein D=

[structure: bicyclic imide with (R₁)ⱼ substituents and G bridge]

wherein G=—CH₂—, —O—, —S—, —SO₂—, —SO—, —CO—, —CHR—, or —CR₂—.

$R_1$=lower alkyl, aryl, substituted alkyl, substituted aryl, lower alkoxy, aryloxy, halogen, or mixtures thereof;

j=0, 1 or 2;

R=hydrogen, lower alkyl, or phenyl.

61. A composition containing a liquid molding compound having the general formula:

$$\left[ (D)_i \text{—} \underset{N}{\overset{N}{\bigcirc}} \text{—} Q \right]_w$$

wherein i=2;

w=2 or 3;

D=a hydrocarbon radical having an unsaturated functionality selected from the group consisting of:

[structures showing various imide-containing hydrocarbon radicals with (R₁)ⱼ substituents]

$R_1$=lower alkyl, aryl, substituted alkyl, substituted aryl, lower alkoxy, aryloxy, halogen, or mixtures thereof;

G=—CH₂—, —O—, —S—, —SO₂—, —SO—, —CO—, —CHR—, or —CR₂—;

j=0, 1 or 2;

T=allyl or methallyl;

Me=methyl;

Q=a hydrocarbon residue containing aliphatic groups connected by ether, ester, urethane, urea, amide, or imide linkages; and R=hydrogen, lower alkyl, or phenyl, wherein the compound can be used in injection molding without the need of solvents.

62. The composition of claim 61 wherein the liquid molding compound has a formula weight less than about 5000.

63. The composition of claim 62 further comprising an alkyl amine diluent.

64. The composition of claim 61 wherein D=

[structure: norbornene-fused imide]

65. A composition containing a liquid molding compound having the general formula $(D)_i$—$R_2$—NHCONH—$R_1$—NHCONH—$R_2$—$(D)_i$ wherein i=1 or 2

D a hydrocarbon radical having an unsaturated functionality which is

[structures showing various imide-containing hydrocarbon radicals]

$R_2$=an aliphatic or aromatic residue of a diamine, and $R_1$=an aliphatic or aromatic residue wherein the compound can be used in injection molding without the need of solvents.

66. The composition of claim 65 wherein i=2

D=a hydrocarbon radical having an unsaturated functionality selected from the group consisting of:

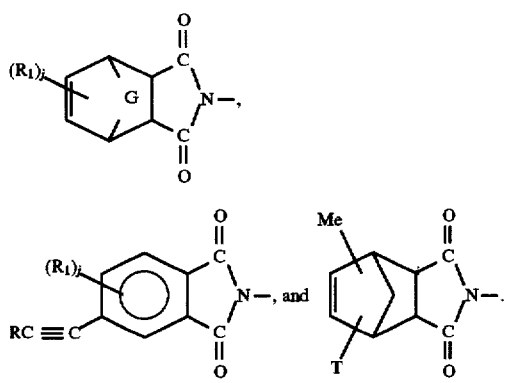

R₁=lower alkyl, aryl, substituted alkyl, substituted aryl, lower alkoxy, aryloxy, halogen, or mixtures thereof;
j=0, 1 or 2;
T=allyl or methallyl; and
Me=methyl.

67. A compound of the formula:

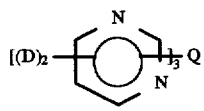

wherein φ=phenylene
Q=a hydrocarbon residue containing aliphatic groups connected by ether linkages

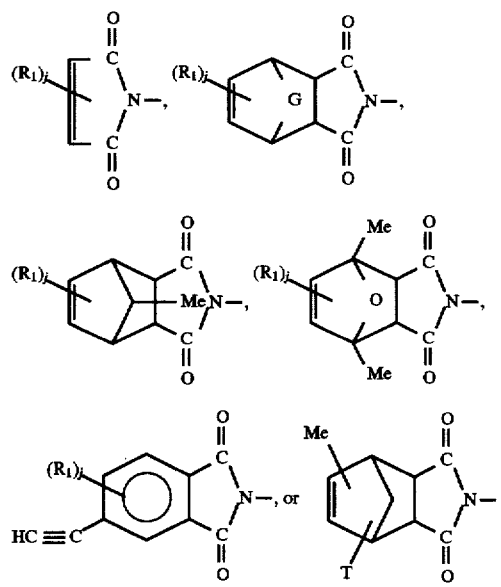

R₁=lower alkyl, aryl, substituted alkyl, substituted aryl, lower alkoxy, aryloxy, halogen, or mixtures thereof;
G=—CH₂—; —O—, —S—, SO₂—, —SO—, —CO—, —CHR—, or —C(R)₂—;
j=0, 1 or 2;
T=allyl or methallyl:
Me=methyl; and
R=hydrogen, lower alkyl, or phenyl.

* * * * *